US008563263B2

(12) United States Patent
Fernholz et al.

(10) Patent No.: US 8,563,263 B2
(45) Date of Patent: *Oct. 22, 2013

(54) ENHANCEMENT OF VANADIUM-CONTAINING PHOSPHATASE INHIBITORS

(75) Inventors: Erhard Fernholz, Weilheim (DE); Dorothea Mayr, Peissenberg (DE)

(73) Assignee: Roche Diagnostics Operations Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/597,606

(22) Filed: Aug. 29, 2012

(65) Prior Publication Data

US 2012/0329134 A1    Dec. 27, 2012

Related U.S. Application Data

(62) Division of application No. 13/070,558, filed on Mar. 24, 2011, now Pat. No. 8,278,086, which is a division of application No. 12/017,115, filed on Jan. 21, 2008, now Pat. No. 8,008,035.

(30) Foreign Application Priority Data

Jan. 25, 2007 (EP) .................................. 07001593

(51) Int. Cl.
*C12Q 1/42* (2006.01)
*G01N 33/53* (2006.01)
*C01G 31/02* (2006.01)

(52) U.S. Cl.
USPC ............................ 435/21; 435/7.8; 423/594.8

(58) Field of Classification Search
USPC .................................. 435/21, 7.8; 423/594.8
See application file for complete search history.

(56) References Cited

U.S. PATENT DOCUMENTS

| 4,976,921 | A | 12/1990 | Itagaki et al. |
| 5,776,714 | A | 7/1998 | Snoke |
| 5,858,648 | A | 1/1999 | Steel et al. |
| 6,299,865 | B1 | 10/2001 | Styczynski et al. |
| 2006/0252683 | A1 | 11/2006 | Lim Tung |

FOREIGN PATENT DOCUMENTS

| CA | 2471601 A1 | 7/2003 |
| EP | 0051964 A2 | 5/1982 |
| EP | 0524633 A2 | 1/1993 |
| WO | 99/58097 A2 | 11/1999 |
| WO | 00/57184 A2 | 9/2000 |
| WO | 03/029209 A2 | 4/2003 |
| WO | 2004/052412 A1 | 6/2004 |
| WO | 2005/054257 A1 | 6/2005 |

OTHER PUBLICATIONS

European Search Report issued Jul. 19, 2007 in European Application No. 07001593.8.
European Search Report issued Nov. 30, 2011 for European Application No. 08001165.3.
Cuncic, Cary et al., "Bis(N,N-dimethylhydroxamido)hydroxooxovanadate Inhibition of Protein Tyrosine Phosphatase Activity in Intact Cells Comparison with Vanadate," Biochemical Pharmacology, 1999, pp. 1859-1867, vol. 58, No. 12.
Gil-Puig, C. et al., "Pit-1 is expressed in normal and tumorous human breast and regulates GH secretion and cell proliferation," European Journal of Endocrinology, 2005, pp. 335-344, vol. 153.
Huyer, Gregory et al., "Mechanism of Inhibition of Protein-Tyrosine Phosphatases by Vanadate and Pervanadate," The Journal of Biological Chemistry, Jan. 10, 1997, pp. 843-851, vol. 272, No. 2.
Ko, Young Hee et al., "Signal transduction to mitochondrial ATP synthase: Evident that PDGF-dependent phosphorylation of the o-subunit occurs in several cell lines, involves, tyrosine, and is modulated by lysophosphatidic acid," Mitochondrion, 2002, pp. 339-348, vol. 1.
Le Bail, J.C. et al., "Estrogenic and antiproliferative activities on MCF-7 human breast cancer cells by flavanoids," Cancer Letters, 1998, pp. 209-216, vol. 130.
Lochhead, Pamela A. et al., "5-Aminoimidazole-4-Carboxamide Riboside Mimics the Effects of Insulin on the Expression of the 2 Key Gluoconeogenic Genes PEPCK and Glucose-6-Phosphatase," Diabetes, Jun. 2000, pp. 896-903, vol. 49.
Naz, Rubina et al., "An 18 kDa Acid Phosphatase from Chicken Heart Possesses Phosphotransferase Activity," The Protein Journal, Feb. 2006, pp. 135-146, vol. 25, No. 2.
Nxumalo, Fikile et al., "Kinetics and molecular modelling studies of the inhibition of protein tyrosine phosphatases by N,N-dimethylhydroxylamine complexes of vanadium (V)," Journal of Biological and Inorganic Chemistry, 1998, pp. 534-542, vol. 3.
Stankiewicz, Paul J. et al., "Inhibition of Phosphate-Metabolizing Enzymes of Oxovanadium(V) Complexes," Metal Ions in Biological Systems, 1993, pp. 287-324, vol. 31.

*Primary Examiner* — Susan Hanley
*Assistant Examiner* — Paul Martin
(74) *Attorney, Agent, or Firm* — Faegre Baker Daniels LLP

(57) ABSTRACT

The present invention is directed to a composition comprising a vanadium-containing phosphatase inhibitor and a polyol. In the presence of the polyol the effect of the inhibitor is enhanced, even in the presence of chelating agents or reducing agents. The invention also concerns the use of the inventive composition for inhibiting a phosphatase, as well as kits comprising the composition.

8 Claims, 5 Drawing Sheets

SEQUENCE LISTING

```
<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (9)..(9)
<223> OTHER INFORMATION: Phosphotyrosine

<400> SEQUENCE: 1

Arg Arg Leu Ile Glu Asp Ala Glu Tyr Ala Ala Arg Gly
 1               5                  10
```

ENHANCEMENT OF VANADIUM-CONTAINING PHOSPHATASE INHIBITORS

This application is a divisional application of U.S. application Ser. No. 13/070,558 filed Mar. 24, 2011 which issued as U.S. Pat. No. 8,278,086 on Oct. 2, 2012, which is a divisional application of U.S. application Ser. No. 12/017,115 filed Jan. 21, 2008 which issued as U.S. Pat. No. 8,008,035 on Aug. 30, 2011, and claims priority to European application No. EP 07001593.8 filed Jan. 25, 2007.

The present invention relates to the biochemistry of phosphatases. Particularly, the invention deals with compounds which can be used as additives alongside vanadium-containing inhibitors of different phosphatase enzymes. The additive compounds according to the invention provide an enhancement of the inhibitory effect. As a consequence, lower concentrations of vanadium containing compounds can be used to achieve a sufficient inhibition of phosphatases.

BACKGROUND OF THE INVENTION

A phosphatase is an enzyme that hydrolyzes phosphoric acid monoesters into a phosphate ion and a molecule with a free hydroxyl group. This action is directly opposite to that of phosphorylases and kinases, which attach phosphate groups to their substrates by using chemical energy conserving molecules like ATP.

Phosphatases can be categorized into two main categories: metalloenzymes (which are dependent on the presence of two or more metal ions in their active sites for activity), and non-metalloenzymes. These categories can then be divided into further sub-categories. The metalloenzymes by far comprise the greatest bulk of phosphatases and contain such enzymes as alkaline phosphatase (three metal ions, only two of which are catalytically active), the serine threonine phosphatases, and inositol monophosphatase. Best known of the non-metalloenzymes are the protein tyrosine phosphatases, which hydrolyze phospho-tyrosine residues.

The presence or absence of a phosphate group on proteins is known to play a regulatory role in many biochemical and particularly signal transduction pathways. Tyrosine residues can be tagged with a phosphate group (phosphorylated) by protein kinases. In its phosphorylated state, the tyrosine residue is referred to as phosphotyrosine. Tyrosine phosphorylation is considered as one of the key steps in signal transduction and regulation of enzymatic activity. Phosphotyrosine can be detected through specific antibodies. Together, specialized kinases and phosphatases regulate the activity of enzymes, receptors and other components of signal transduction pathways, transcription factors, and other functional proteins.

Thus, there are numerous biochemical methods aimed at detecting phosphorylated proteins in a biological sample. For instance, sampled cell material is lysed and the protein fraction is subjected to one-dimensional (e.g., SDS-PAGE) or two-dimensional (e.g., $1^{st}$ dimension: isoelectric focussing, $2^{nd}$ dimension: SDS PAGE) separation, and phosphorylated proteins of individual bands or spots are detected by phosphoserine- or phosphotyrosine-specific antibodies. Other more specific detection methods make use of antibodies which specifically bind to particular phosphorylated proteins. Such antibodies are frequently used for histocytochemical detection of phosphorylated target proteins in formalin fixed paraffin embedded tissue sections from biopsy material.

Regardless of the detection method used, the result of the analysis of phosphorylated proteins is desired to reflect the status of phosphorylation at the time point when the experiment is started, that is to say when the cells are lysed or the tissue is fixed and sectioned. More generally, it is desired to conserve the status of protein phosphorylation at a certain point in time. Conservation is achieved by preventing phosphate esters to be hydrolyzed from their target proteins. To this end, the state of the art provides a number of substances capable of inhibiting phosphatase activity. Inhibitors are applied routinely when performing assays for the detection of phosphorylated proteins but also when phosphorylated proteins are to be purified in larger amounts.

Among vanadium-containing inhibitors of phosphatase activity, pervanadate and vanadate are the best known and most widely employed substances. Vanadate is a phosphate analogon which mimics the transition state of phosphate hydrolysis and is therefore considered as a general phosphatase inhibitor. However, vanadate is recognized to be particularly suited to inhibit tyrosine phosphatases (Huyer, G., et al., J. Biol. Chem. 272 (1997) 843-851) and alkaline phosphatases (e.g., Stankiewicz, P. J., et al., in Met. Ions Biol. Syst. 31 (1995) 287-324). But inhibition of other phosphatase like ATPases, glucose-6 phosphatase, acid phosphatase, or fructose-2,6-bisphosphatase had also been reported.

However, a disadvantage is that in order to provide an effective amount, vanadate has to be in a concentration in the micromolar or even millimolar range. In this regard, an "effective amount" is understood as being between 1× (one time) and 50× (fifty times) the concentration of the inhibitor in an aqueous solution which at a 1× concentration reduces the activity of a phosphatase by the factor of 20. In contrast to vanadate, other inhibitors of phosphatase activity are known which are effective at nanomolar concentrations. An example therefor is cantharidin.

It has been reported, however, that the inhibitory effect can be enhanced by way of forming stable vanadate-containing complexes. E.g., potassium bisperoxo (bipyridine) oxovanadate (V) and potassium bisperoxo (1,10 phenanthroline) oxovanadate (V)) both are more potent than orthovanadate. However, complexation of vanadate it not necessarily a prerequisite for improvement of potency. For instance, hydroxylamine or dimethylhydroxylamine spontaneously form complexes with vanadate. The potency of those complexes remain the same or is reduced to a certain extent (Cuncic, C., et al., Biochem. Pharmacol. 58 (1999) 1859-1867). In cell-based assays, it was found that these two compounds increase the uptake of vanadate into the cellular lumen (Nxumalo, F., et al., J. Biol. Inorg. Chem. 3 (1998) 534-542; Cuncic, C., et al., Biochem. Pharmacol. 58 (1999) 1859-1867).

It is further known that in the presence of certain complex-forming reagents like EDTA, the phosphatase inhibiting effect of vanadate is reduced by a factor of about 1,000 (Huyer, G., et al., J. Biol. Chem. 272 (1997) 843-851). This is particularly disadvantageous because EDTA is frequently used in biochemistry as a stabilizer and as an inhibitor of metalloenzymes such as phosphatases and proteases. Another important stabilizer for use in the preparation of cell lysates is dithiothreitol (DTT). The inventors have found that DTT also reduces to a significant extent the inhibitory effect of vanadate on phosphatases.

In view of the disadvantages of the state of the art, it is an object of the present invention to provide alternative compounds which enhance the inhibitory effect of vanadate-containing compounds on enzymes with phosphatase activity. It is another object of the invention to provide compounds which counteract the negative effects of EDTA and DTT on vanadate-containing compounds.

The inventors have surprisingly found that in the presence of a polyol the inhibitory effect of vanadate on phosphatases and particularly on phosphotyrosine-specific phosphatases is potentiated. This effect was observed even with a very simple polyol like glycerol but also with sugar alcohols like mannitol. Even more surprising, the negative effects of EDTA and DTT on vanadate were found to be reduced significantly or even abolished completely.

SUMMARY OF THE INVENTION

A first embodiment of the invention is the use of a composition comprising (i) an ionic compound selected from the group consisting of vanadyl (II), vanadate (IV), vanadate (V), oligomeric vanadate (V), and mixtures thereof, and (ii) a polyol, for inhibiting an enzyme with phosphatase activity. A second embodiment of the invention is a composition comprising (i) an ionic compound selected from the group consisting of vanadyl (II), vanadate (IV), vanadate (V), oligomeric vanadate (V), and mixtures thereof, and (ii) a polyol, characterized in that the molar ratio of the polyol to the vanadate-containing compound is equal to or greater than 1:1. A third embodiment of the invention is a method for inhibiting an enzyme with phosphatase activity, comprising the steps of (a) dissolving in an aqueous solvent a composition comprising (i) an ionic compound selected from the group consisting of vanadyl (II), vanadate (IV), vanadate (V), oligomeric vanadate (V), and mixtures thereof, and (ii) a polyol, and (b) contacting the enzyme with phosphatase activity with the solution of step (a). A fourth embodiment of the invention is a kit of parts comprising packaging material and a composition containing a composition with (i) an ionic compound selected from the group consisting of vanadyl (II), vanadate (IV), vanadate (V), oligomeric vanadate (V), and mixtures thereof, and (ii) a polyol.

DETAILED DESCRIPTION OF THE INVENTION

Figure 1:
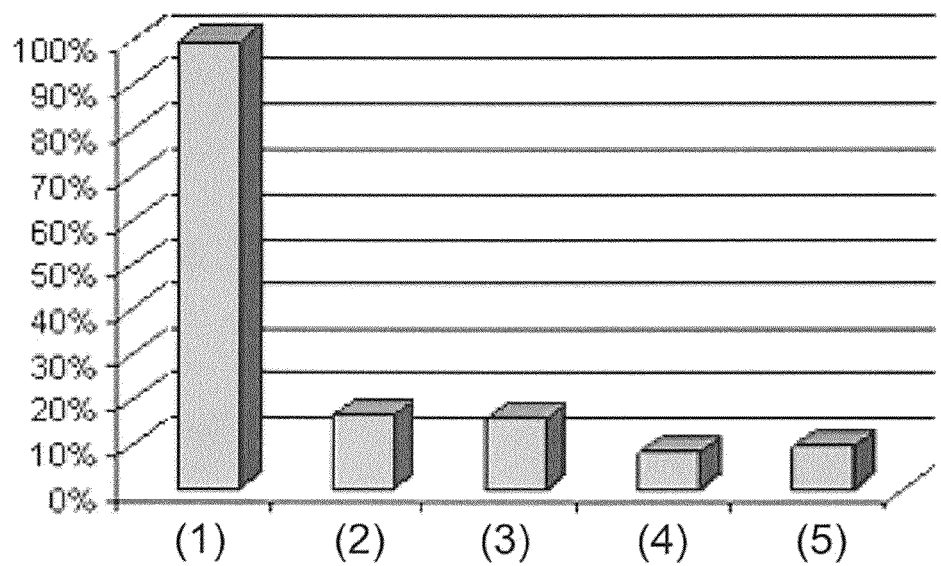
FIG. 1 Inhibition of a phosphotyrosine-specific protein phosphatase with orthovanadate in the presence or absence of a polyol. For the principle of the experiment reference is made to Example 1. The ordinate indicates residual phosphatase activity. The bars indicate the results obtained for the following compositions: (1) no inhibitor added (control, 100% residual activity); (2) 1 mM orthovanadate; (3) 2 mM orthovanadate; (4) 1 mM orthovanadate, 27 mM mannitol; (5) 1 mM orthovanadate, 54 mM glycerol.

Certain terms are used with particular meaning, or are defined for the first time, in this description of the present invention. For the purposes of understanding the present invention, the terms used to describe the invention are defined by their art-accepted definitions, when such exist, except that when those definitions conflict or partially conflict with the definitions set forth below. In the event of a conflict in definition, the meaning of the terms are first defined by the definitions set forth below.

The term "comprising" is used in the description of the invention and in the claims to mean "including, but not necessarily limited to". The indefinite article "a" in combination with a term denoting a chemical compound such as an inhibitor or an additive is used to denote "one or more". A "phosphatase inhibitor" is a substance which is effective to inhibit the hydrolysis of phosphoesters by phosphatase enzymatic activity, and thereby the release of phosphate ions from a target molecule. An "aqueous" solution is understood as a solution wherein the liquid solvent is an aqueous solvent which comprises at least 80% [v/v] water, more preferred 95% [v/v], even more preferred 99% [v/v], yet even more preferred 100% [v/v]. The skilled person appreciates that the solution further comprises one or more further compounds such as a salt, a buffer, an inhibitor, an additive, and a biological molecule, whereby the one or more compounds are dissolved in the liquid solvent.

The composition according to the invention comprises an ionic compound selected from the group consisting of vanadyl (II), vanadate (IV), vanadate (V), oligomeric vanadate (V), and mixtures thereof. Very much preferred, the ionic vanadium-containing compound is orthovanadate (V) and oligomers thereof. A preferred oligomer is selected from the group consisting of a di-, tri-, and tetravananadate ion. Another very much preferred ionic compound in the composition according to the invention is a peroxovanadate ion. However, most preferred is orthovanadate ($VO_4^{3-}$).

The "polyol" in the composition according to the invention is a water-soluble organic compound in which two or more hydroxyl groups are covalently linked with carbon atoms. It is preferred that two of the hydroxyl groups of the polyol according to the invention are bonded to two adjacent carbon atoms. In other words, the preferred polyol comprises two vicinal hydroxyl groups. However, polyols with more than two vicinal hydroxyl groups are preferred. Very well known and very much preferred polyols with vicinal hydroxyl groups are sugar alcohols. A "sugar alcohol" is a hydrogenated form of carbohydrate, whose carbonyl group (aldehyde or ketone) has been reduced to a primary or secondary hydroxyl group. The unhydrogenated form of the carbohydrate is also referred to as a "reducing" sugar.

The composition according to the invention preferably comprises a sugar alcohol with 4-100 carbon atoms. In this respect, non-reducing mono-, di-, tri- and tetrasaccharides are very much preferred.

A very much preferred sugar alcohol is a non-reducing monosaccharide. Such a sugar alcohol can be a C4 sugar alcohol and is preferably selected from the group consisting of threitol and eythritol. Also very much preferred, the sugar alcohol is a C5 sugar alcohol and preferably selected from the group consisting of ribitol, arabitol, xylitol, and lyxitol. Also very much preferred, the sugar alcohol is a C5 deoxy sugar alcohol and preferably selected from the group consisting of deoxyribitol and deoxyarabitol. Also very much preferred, the sugar alcohol is a C6 sugar alcohol and preferably selected from the group consisting of allitol, altritol, mannitol, glucitol, gulitol, iditol, galactitol, and talitol.

According to the invention, a deoxy sugar alcohol is encompassed by the term sugar alcohol provided that the deoxy sugar provides four or more pairs of vicinal hydroxyl groups. A very much preferred sugar alcohol is a C6 deoxy sugar alcohol preferably selected from the group consisting of deoxyglucitol, and deoxy-mannitol. Also very much preferred, the sugar alcohol is a sugar alcohol with other substituents in the C2-position, of which a preferred example is N-acetyl glucitol amine 2 with other substituents on C2-position like N-acetyl glucitol amine-2.

Disaccharides and monosaccharides can both form sugar alcohols; however, sugar alcohols derived from disaccharides (e.g., maltitol and lactitol) are not entirely hydrogenated because, due to the glycosidic bond, only one aldehyde group is available for reduction. The same applies to trisaccharides and higher saccharides. Thus a non-reducible di- or trisaccharide or a non-reducing higher oligosaccharide with up to 100 C atoms can be used with great advantage to practice the invention. Sucrose is a highly preferred sugar alcohol. What is noteworthy about sucrose is that, unlike most polysaccharides, the glycosidic bond is formed between the reducing ends of both glucose and fructose and not between the reducing end of one and the nonreducing end of the other. The effect of this inhibits further bonding to other saccharide units. Since it contains no free anomeric carbon atom, it is a non-reducing sugar.

According to the invention, the preferred molar ratio between the polyol and the ionic vanadium-containing compound is higher than 1:1. Very much preferred, the molar ratio is between 100:1 and 1:1. Even more preferred, the molar ratio is between 70:1 and 5:1. Even more preferred, the molar ratio is between 50:1 and 10:1.

Taking phosphatase activity in a sample in the absence of a vanadium containing inhibitor as a reference (100%), the combination of an ionic compound selected from the group consisting of vanadyl (II), vanadate (IV), vanadate (V), oligomeric vanadate (V) and a polyol according to the invention, when added to the sample, is capable of substantially reducing said phosphatase activity. Typically, said activity is reduced to a value between 1.5% and 40%, more typically to a value of between 1.5% and 30%, even more typically to a value of between 1.5% and 20%, even more typically to a value of between 1.5% and 10%.

On the one hand, the polyol enhances the inhibitory effect of the ionic vanadium-containing compound on phosphatase activity. On the other hand, the polyol reduces the negative effect of complex-forming agents. That is to say inhibition of phosphatase activity is not adversely affected by the presence of a chelating agent for divalent or trivalent positively charged metal ions. Complex formation of divalent ions may therefore, e.g., prevent undesired activity of a number of proteases without side effects. For this reason, the composition of the invention additionally comprises a chelating agent for divalent or trivalent positively charged metal ions. A preferred chelating agent is selected from the group consisting of EDTA, citrate, EGTA, and 1,10-phenanthroline. The preferred concentration of the chelating agent in the composition according to the invention is between 0.1 mM and 50 mM, more preferred between 0.2 mM and 10 mM, and most preferred at about 1 mM.

Furthermore, the polyol in the composition reduces the negative effect of reducing agents on the ionic vanadium-containing compound. Particularly DTT reduces the inhibition of phosphatase activity by orthovanadate. However, in the presence of a polyol the reduction is reversed. A preferred reducing agent is selected from the group consisting of DTT (dithiothreitol), beta-mercaptoethanol, glutathione, and thioredoxine. The preferred concentration of the reducing agent in the composition according to the invention is between 0.1 mM and 30 mM, more preferred between 0.2 mM and 10 mM, and most preferred at about 1 mM.

In another embodiment of the invention, the composition is provided for the end-user in a convenient form. An example therefor is a package containing a measured quantity of the composition. The packaging material is preferably selected to prevent contact with water or water vapour. In addition, one or more packages can be stored in the presence of drying material such as silica gel or other suitable substances. The composition can be in the form of a free-flowing granulate. Even more preferred, the composition is in the form of a tablet. In this case, the composition may in addition contain further materials which facilitate tablet formation.

In addition, the composition of the invention may contain one or more additional phosphatase inhibitors which is a compound other than a vanadium-containing compound. The one or more additional phosphatase inhibitors is preferably an ionic inhibitor like NaF. Also preferred, the inhibitor is a low molecular weight compound selected from the group consisting of canthridin, napthyl phosphate, and microcystin. Also preferred, the inhibitor is a peptidic compound selected from the group consisting of calcineurin autoinhibitory peptide and protein phosphatase inhibitor 2.

Owing to the surprising effect of the presence of a polyol in addition to the vanadate-containing compound, the composition according to the invention is suitable for the inhibition of an enzyme with phosphatase activity. The composition is particularly suited to inhibit a phosphatase selected from the group consisting of an acid phosphatase, an alkaline phosphatase, a phospho tyrosine phosphatase, an ATPase, a phosphoserin/threonin phosphatase, and a dual phosphatase. Most preferred, the composition is used to inhibit a protein tyrosine phosphatase, that is to say to hydrolyze the phosphate ester of a phosphotyrosine residue, whereby the phosphotyrosine residue is part of a phosphorylated polypeptide. Examples for polypeptides which may contain a phosphorylated tyrosine residue and which are a substrate for a phosphotyrosine-specific protein phosphatase are the phosphorylated receptor of erythropoietin, pErk1, pErk2, and pJak2.

Another embodiment of the invention is thus a method to inhibit an enzyme with phosphatase activity comprising the steps of (a) dissolving in an aqueous solvent a composition comprising (i) an ionic compound selected from the group consisting of vanadyl (II), vanadate (IV), vanadate (V), oligomeric vanadate (V), and mixtures thereof, and (ii) a polyol, and (b) contacting the enzyme with phosphatase activity with the solution of step (a).

A further embodiment of the invention is therefore a liquid composition comprising the composition according to the invention and an aqueous solvent. The pH of the liquid composition preferably corresponds to a pH value at which a phosphatase enzyme (one or more target phosphatases) is active. The pH is preferably in the range of pH 5.5-pH 8.5, more preferred in the range of pH 6.7-pH 8.0.

The following examples and figures are provided to aid the understanding of the present invention, the true scope of which is set forth in the appended claims. It is understood that modifications can be made in the procedures set forth without departing from the spirit of the invention.

Example 1

Inhibition of a Phosphotyrosine-Specific Protein Phosphatase

A stock solution of a recombinantly produced phosphotyrosine-specific protein phosphatase (human T-cell; Calbiochem, No. Cat 539732) was diluted in the ratio of 1:200 in a buffer containing 0.1 mM $CaCl_2$, 50 mM Tris pH 7.0. In separate reaction tubes the following mixtures (a-e) were prepared: 36 µl of diluted enzyme solution and 4 µl of either of (a) water (as a reference for 100%) one solution of (b) 10 mM orthovanadate; (c) 20 mM orthovanadate; (d) 10 mM orthovanadate, 270 mM mannitol; (e) 10 mM orthovanadate, 540 mM glycerol. Each mixture was incubated at room temperature (RT) for 15 min. Subsequently, an aliquot of 10 µl was transferred from each mixture to a microwell plate. 5 µl of a solution of a test peptide containing a phosphotyrosine residue (the peptide having the sequence R-R-L-I-E-D-A-E-pY-A-A-R-G (SEQ ID NO: 1); 1 mM in water) and 10 µl of a buffer containing 0.1 mM $CaCl_2$, 50 mM Tris pH 7.0 were added to each well and incubated for 30 min at 37° C. Free phosphate resulting from enzymatic hydrolysis of the phosphoester bond was subjected to a detection reaction following the addition of 100 µl of a 1 M HCl solution additionally containing 0.034% [w/v] malachite green, 10 mM sodium molybdate, and 3.4% [v/v] ethanol. The detection reaction was performed for 10 min at RT while constantly agitating the microwell plate. Relative concentrations of phosphate were detected following the determination of the extinction (620 nm) of each reaction well.

Example 2

Inhibition of a Phosphotyrosine-Specific Protein Phosphatase in the Presence of EDTA and DTT A stock solution of a recombinantly produced phosphotyrosine-specific protein phosphatase (human T-cell; Calbiochem, No. Cat 539732) was diluted in the ratio of 1:200 in a buffer containing 25 mM Hepes, 50 mM NaCl, 2.5 mM EDTA, 5 mM DTT, pH 7.2. In separate reaction tubes the following mixtures (a-e) were prepared: 36 µl of diluted enzyme solution and 4 µl of either of (a) water (as a reference for 100%) one solution of (b) 10 mM orthovanadate; (c) 20 mM orthovanadate; (d) 10 mM orthovanadate, 270 mM mannitol; (e) 10 mM orthovanadate, 540 mM glycerol. Each mixture was incubated at room temperature (RT) for 15 mM. Subsequently, an aliquot of 10 µl was transferred from each mixture to a microwell plate. 5 µl of a solution of a test peptide containing a phosphotyrosine residue (the peptide having the sequence R-R-L-I-E-D-A-E-pY-A-A-R-G (SEQ ID NO: 1); 1 mM in water) and 10 µl of a buffer containing 25 mM Hepes, 50 mM NaCl, 2.5 mM EDTA, 5 mM DIT, pH 7.2 were added to each well and incubated for 30 min at 37° C. Free phosphate resulting from enzymatic hydrolysis of the phosphoester bond was subjected to a detection reaction following the addition of 100 µl of a 1 M HCl solution additionally containing 0.034% [w/v] malachite green, 10 mM sodium molybdate, and 3.4% [v/v] ethanol. The detection reaction was performed for 10 min at RT while constantly agitating the microwell plate. Relative concentrations of phosphate were detected following the determination of the extinction (620 nm) of each reaction well.

Example 3

Inhibition of a Phosphotyrosine-Specific Protein Phosphatase in the Presence of EDTA, whereby DTT is Either Present Additionally or Absent A stock solution of a recombinantly produced phosphotyrosine-specific protein phosphatase (human T-cell; Calbiochem, No. Cat 539732) was diluted in the ratio of 1:200, either in a buffer containing 25 mM Hepes, 50 mM NaCl, 2.5 mM EDTA, 5 mM DTT, pH 7.2 (enzyme solution (i)) or in a buffer with the same composition but without DTT (enzyme solution (ii)). In separate reaction tubes the following mixtures (a-f) were prepared: 36 µl of either diluted enzyme solution (i) or (ii) and 4 it of either one solution of (a, d) 10 mM orthovanadate; (b, e) 10 mM orthovanadate, 270 mM mannitol; (c, f) 10 mM orthovanadate, 540 mM glycerol. Each mixture was incubated at room temperature (RT) for 15 min. Subsequently, an aliquot of 10 µl was transferred from each mixture to a microwell plate. 5 µl of a solution of a test peptide containing a phosphotyrosine residue (the peptide having the sequence R-R-L-I-E-D-A-E-pY-A-A-R-G (SEQ ID NO: 1); 1 mM in water) and either 10 µl of a buffer containing 25 mM Hepes, 50 mM NaCl, 2.5 mM EDTA, 5 mM DTT, pH 7.2 (reactions with enzyme solution (i)) or 10 µl of a buffer containing 25 mM Hepes, 50 mM NaCl, 2.5 mM EDTA, pH 7.2 (reactions with enzyme solution (ii)) were added to each well and incubated for 30 min at 37° C. Free phosphate resulting from enzymatic hydrolysis of the phosphoester bond was subjected to a detection reaction following the addition of 100 µl of a 1 M HCl solution additionally containing 0.034% [w/v] malachite green, 10 mM sodium molybdate, and 3.4% [v/v] ethanol. The detection reaction was performed for 10 min at RT while constantly agitating the microwell plate. Relative concentrations of phosphate were detected following the determination of the extinction (620 nm) of each reaction well.

Example 4

Inhibition of a Phosphotyrosine-Specific Protein Phosphatase with Orthovanadate

TABLE 1

Residual phosphatase activity in the presence of compositions containing orthovanadate and other compounds in aqueous buffers as indicated. The tabulated data refer to the graphic representations given in FIGS. 1-3.

Figure 2:
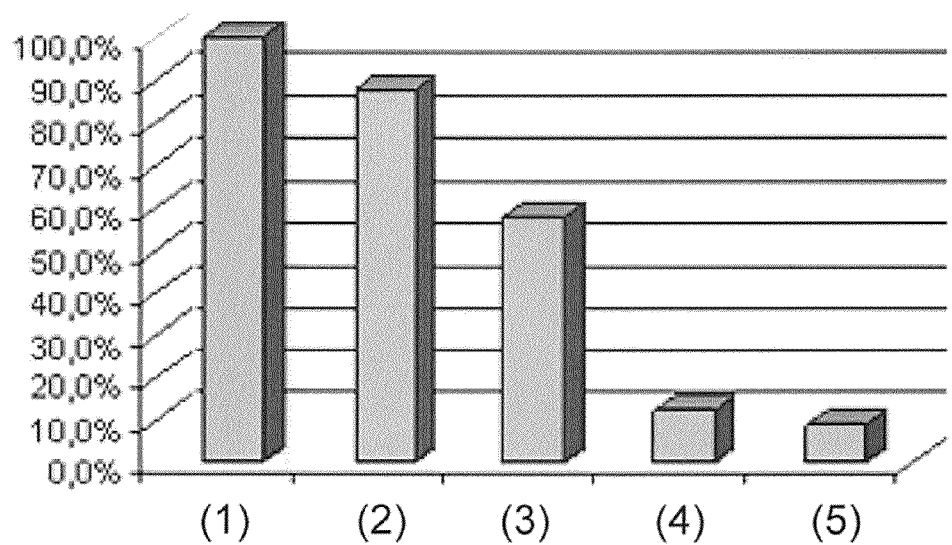
FIG. 2 Inhibition of a phosphotyrosine-specific protein phosphatase with orthovanadate in the presence or absence of a polyol and in the presence of EDTA and DTT. For the principle of the experiment reference is made to Example 2. The ordinate indicates residual phosphatase activity. The bars indicate the results obtained for the following compositions: (1) no inhibitor added (control, 100% residual activity); (2) 1 mM orthovanadate; (3) 2 mM orthovanadate; (4) 1 mM orthovanadate, 27 mM mannitol; (5) 1 mM orthovanadate, 54 mM glycerol.

| | Buffer | Activity |
|---|---|---|
| FIG. 1: | | |
| 1) Without Inhibitor | 50 mM Tris; 0.1 mM $CaCl_2$ pH 7.0 | 100% |
| 2) $Na_3VO_4$ 1 mM | 50 mM Tris; 0.1 mM $CaCl_2$ pH 7.0 | 16.6% |
| 3) $Na_3VO_4$ 2 mM | 50 mM Tris; 0.1 mM $CaCl_2$ pH 7.0 | 15.7% |
| 4) $Na_3VO_4$ 1 mM + mannitol 27 mM | 50 mM Tris; 0.1 mM $CaCl_2$ pH 7.0 | 8.5% |
| 5) $Na_3VO_4$ 1 mM + glycerol 54 mM | 50 mM Tris; 0.1 mM $CaCl_2$ pH 7.0 | 9.7% |
| FIG. 2: | | |
| 1) Without Inhibitor | 25 mM Hepes; 50 mM NaCl; 2.5 mM EDTA; 5 mM DTT pH 7.2 | 100% |
| 2) $Na_3VO_4$ 1 mM | 25 mM Hepes; 50 mM NaCl; 2.5 mM EDTA; 5 mM DTT pH 7.2 | 87.7% |

TABLE 1-continued

Residual phosphatase activity in the presence of compositions containing orthovanadate and other compounds in aqueous buffers as indicated. The tabulated data refer to the graphic representations given in FIGS. 1-3.

Figure 3:
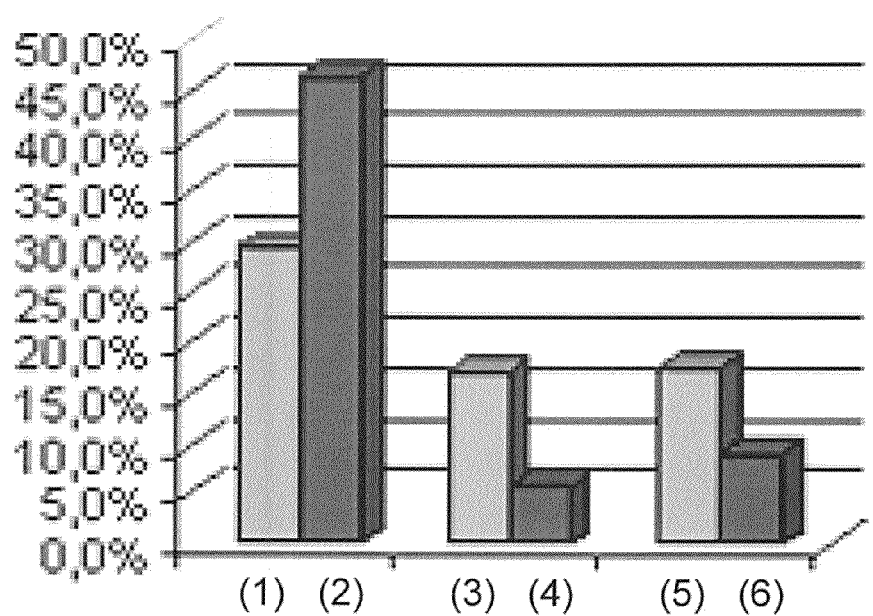
FIG. 3 Inhibition of a phosphotyrosine-specific protein phosphatase with orthovanadate in the presence or absence of a polyol and in the presence of EDTA, with or without DTT. For the principle of the experiment reference is made to Example 3. The ordinate indicates residual phosphatase activity. The bars indicate the results obtained for the following compositions: (1) 1 mM orthovanadate, Hepes buffer with EDTA; (2) 1 mM orthovanadate, Hepes buffer with EDTA and DTT; (3) 1 mM orthovanadate, Hepes buffer with EDTA, in the presence of 27 mM mannitol; (4) 1 mM orthovanadate, Hepes buffer with EDTA and DTT, in the presence of 27 mM mannitol; (5) 1 mM orthovanadate, Hepes buffer with EDTA, in the presence of 54 mM glycerol; (6) 1 mM orthovanadate, Hepes buffer with EDTA and DTT, in the presence of 54 mM glycerol.

| | Buffer | Activity |
|---|---|---|
| 3) $Na_3VO_4$ 2 mM | 25 mM Hepes; 50 mM NaCl; 2.5 mM EDTA; 5 mM DTT pH 7.2 | 58.0% |
| 4) $Na_3VO_4$ 1 mM + mannitol 27 mM | 25 mM Hepes; 50 mM NaCl; 2.5 mM EDTA; 5 mM DTT pH 7.2 | 12.4% |
| 5) $Na_3VO_4$ 1 mM + glycerol 54 mM | 25 mM Hepes; 50 mM NaCl; 2.5 mM EDTA; 5 mM DTT pH 7.2 | 9.3% |
| FIG. 3: | | |
| 1) $Na_3VO_4$ 1 mM | 25 mM Hepes; 50 mM NaCl; 2.5 mM EDTA; pH 7.2 | 29.5% |
| 2) $Na_3VO_4$ 1 mM | 25 mM Hepes; 50 mM NaCl; 2.5 mM EDTA; 5 mM DTT pH 7.2 | 46.3% |
| 3) $Na_3VO_4$ 1 mM + mannitol 27 mM | 25 mM Hepes; 50 mM NaCl; 2.5 mM EDTA; pH 7.2 | 14.1% |
| 4) $Na_3VO_4$ 1 mM + mannitol 27 mM | 25 mM Hepes; 50 mM NaCl; 2.5 mM EDTA; 5 mM DTT pH 7.2 | 5.8% |
| 5) $Na_3VO_4$ 1 mM + glycerol 54 mM | 25 mM Hepes; 50 mM NaCl; 2.5 mM EDTA; pH 7.2 | 14.9% |
| 6) $Na_3VO_4$ 1 mM + glycerol 54 mM | 25 mM Hepes; 50 mM NaCl; 2.5 mM EDTA; 5 mM DTT pH 7.2 | 7.3% |

Example 5

Inhibition of Phosphatases in Insect Cell Lysate 270 mg insect cells (SF9) were collected, washed 3 times with 50 mM Hepes, 50 mM NaCl pH 7.0 and lysed using 2.5 ml M-Per (Pierce) for 10 min. After centrifugation the lysate was collected as the supernatant.

Test for phosphotyrosine activity: To 45 µl of the lysate, 5 µl of either water or orthovanadate (10 mM) or orthovanadate/mannitol (10 mM/270 mM) were added and incubated for 10 min at room temperature.

Subsequently, an aliquot of 10 µl was transferred from each mixture into a well of a microwell plate. 5 µl of a solution of a test peptide (R-R-L-I-E-D-A-E-pY-A-A-R-G (SEQ ID NO: 1); 1 mM in water) and 10 µl of a buffer containing 0.1 mM $CaCl_2$, 50 mM Tris pH 7.0 were added to each well and incubated for 30 min at 37° C. Free phosphate resulting from the enzymatic hydrolysis was then detected via addition of 100 µl of a 1 M HCl solution additionally containing 0.034% [w/v] malachite green, 10 mM sodium molybdate and 3.4% [v/v] ethanol. The detection was performed for 10 min at RT while constantly agitating the microwell plate. Relative concentrations of free phosphate were detected following the determination of the extinction (620 nm) of each reaction well.

TABLE 2

Figure 4:
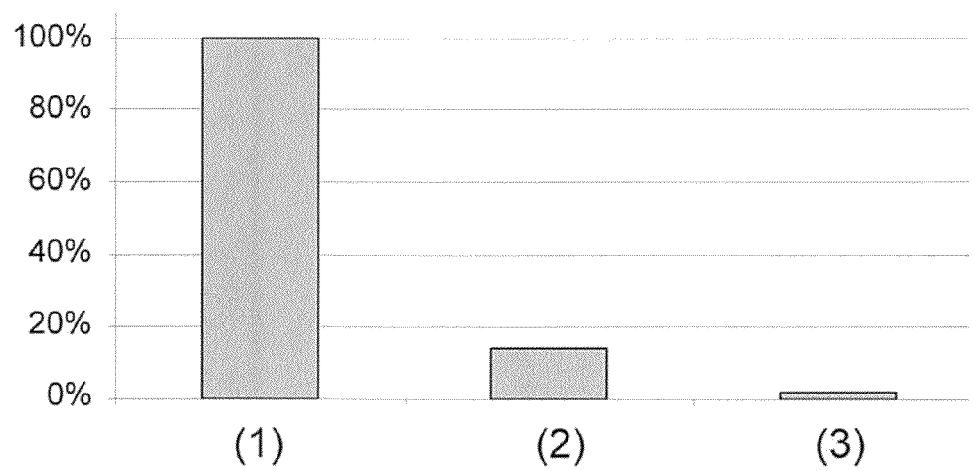
FIG. 4 Inhibition of phosphatase activity in insect cell lysate with orthovanadate in the presence or absence of mannitol. For the principle of the experiment reference is made to Example 5. The ordinate indicates residual phosphatase activity. The bars indicate the results obtained for the following compositions: (1) no inhibitor added (control, 100% residual activity); (2) 1 mM orthovanadate; (3) 1 mM orthovanadate, 27 mM mannitol.

Residual phosphatase activity in the presence of compositions containing orthovanadate and other compounds in aqueous buffers as indicated. The tabulated data refer to the graphic representations given in FIG. 4.

| | Phosphatase activity |
|---|---|
| no inhibitor (water control) | 100% |
| 1 mM orthovandate | 14% |
| 1 mM orthovanadate/27 mM mannitol | 2% |

Example 6

Inhibition of Phosphatases in COS7 Cell Lysate

COS7 cells were collected, washed 3 times with 50 mM Hepes, 50 mM NaCl pH 7.0 and lysed using 5 ml M-Per (Pierce) for 10 min. After centrifugation the lysate was collected as the supernatant.

Test for phosphotyrosine activity: To 45 µl of the diluted lysate (1+4 with M-Per (Pierce)) 5 µl of either water or orthovanadate (10 mM) or orthovanadate/mannitol (10 mM/270 mM) were added and incubated for 10 min at room temperature.

Subsequently, an aliquot of 10 µl was transferred from each mixture to a microwell plate. 5 µl of a solution of a test peptide (R-R-L-I-E-D-A-E-pY-A-A-R-G (SEQ ID NO: 1); 1 mM in water) and 10 µl of a buffer containing 0.1 mM $CaCl_2$, 50 mM Tris pH 7.0 were added to each well and incubated for 30 min at 37° C. Free phosphate resulting from the enzymatic hydrolysis was then detected via addition of 100 µl of a 1M HCl solution additionally containing 0.034% [w/v] malachite green, 10 mM sodium molybdate and 3.4 [v/v] ethanol. The detection was performed for 10 min at RT while constantly agitating the microwell plate. Relative concentrations of free phosphate were detected following the determination of the extinction (620 nm) of each reaction well.

TABLE 3

Figure 5:
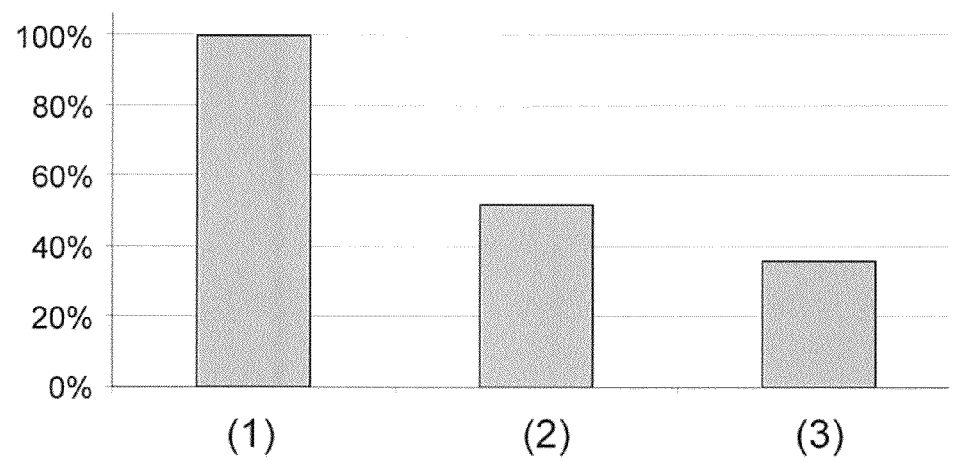
FIG. 5 Inhibition of phosphatase activity in COST cell lysate with orthovanadate in the presence or absence of mannitol. For the principle of the experiment reference is made to Example 6. The ordinate indicates residual phosphatase activity. The bars indicate the results obtained for the following compositions: (1) no inhibitor added (control, 100% residual activity); (2) 1 mM orthovanadate; (3) 1 mM orthovanadate, 27 mM mannitol.

Residual phosphatase activity in the presence of compositions containing orthovanadate and other compounds in aqueous buffers as indicated. The tabulated data refer to the graphic representations given in FIG. 5.

| | phosphatase activity |
|---|---|
| no inhibitor (water control) | 100% |
| 1 mM orthovandate | 52% |
| 1 mM orthovanadate/27 mM mannitol | 36% |

What is claimed is:

1. A composition comprising an aqueous solvent, an enzyme having phosphatase activity, an ionic vanadium-containing inhibitor of phosphatase activity selected from the group consisting of vanadyl (II), vanadate (IV), vanadate (V), and oligomeric vanadate (V), and a polyol selected from the group consisting of mannitol and glycerol, and dithiothreitol, wherein the polyol and the inhibitor are present in a molar ratio of 100:1 to 1:1 (polyol:inhibitor).

2. The composition of claim 1 additionally comprising a chelating agent selected from the group consisting of EDTA, citrate, EGTA, and 1,10-phenanthroline.

3. The composition of claim 1 additionally comprising a reducing agent selected from the group consisting of beta-mercaptoethanol, glutathione, and thioredoxine.

4. The composition of claim 1 wherein the vanadium-containing inhibitor has a concentration between 0.1 mM and 10 mM.

5. The composition of claim 1 wherein the vanadium-containing inhibitor has a concentration between 0.5 mM and 5 mM.

6. The composition of claim 1 wherein the polyol has a concentration in the solution between 1 mM and 100 mM.

7. A kit of parts for use with an enzyme having phosphatase activity, the kit comprising packaging material and a composition comprising an aqueous solvent, an ionic vanadium-containing inhibitor of phosphatase activity selected from the group consisting of vanadyl (II), vanadate (IV), vanadate (V), and oligomeric vanadate (V), and a polyol selected from the group consisting of mannitol and glycerol, and dithiothreitol, wherein the polyol and the inhibitor are present in a molar ratio of 100:1 to 1:1 (polyol:inhibitor).

8. The kit of claim 7 wherein the composition additionally comprises a chelating agent selected from the group consisting of EDTA, citrate, EGTA, and 1,10-phenanthroline.

* * * * *